United States Patent [19]

Hodge

[11] 3,960,898

[45] June 1, 1976

[54] ZEARALANONE-ZEARALANOL PRODUCT

[75] Inventor: Edward B. Hodge, Terre Haute, Ind.

[73] Assignee: Commercial Solvents Corporation, Terre Haute, Ind.

[22] Filed: Feb. 5, 1974

[21] Appl. No.: 439,961

[52] U.S. Cl. ................................ 260/343.2 F
[51] Int. Cl.² ................................. C07D 313/00
[58] Field of Search ..................... 260/343.2 F

[56] References Cited
UNITED STATES PATENTS

| | | | |
|---|---|---|---|
| 3,818,044 | 6/1974 | Young | 260/343.2 |
| 3,839,364 | 10/1974 | Young | 260/343.2 |

OTHER PUBLICATIONS

Kleiderer et al., J. Org. Chem., Vol. 13, (1948), p. 455.

*Primary Examiner*—James A. Patten
*Attorney, Agent, or Firm*—Morton, Bernard, Brown, Roberts & Sutherland

[57] ABSTRACT

The high-melting diastereoisomer of zearalanol or derivative thereof is prepared by heating its corresponding low-melting diastereoisomer under dehydrogenating conditions in the presence of a Raney nickel catalyst and under an oxygen-free atmosphere, and then subjecting the solution to reducing conditions under a hydrogen atmosphere at elevated pressure.

16 Claims, No Drawings

ZEARALANONE-ZEARALANOL PRODUCT

This invention relates to a method of producing a high melting diastereoisomer of zearalanol or a derivative of it from its corresponding low melting diastereoisomer. The term zearalanol conforms to the nomenclature in an article by Johnston et al., "Synthesis of Dideoxy Zearalanone and Hydroxyl Derivatives", Journal of Medicinal Chemistry, Volume 13, No. 5 (1970), page 941.

Compounds whose molecules contain the same number and kind of atoms arranged in the molecule in an identical manner except for the relative positions are termed stereoisomers. Two stereoisomers are called enantiomorphs or enantiomers when they are mirror image, have no plane of symmetry, and essentially differ only with respect to the direction in which they rotate the plane of polarized light, the angle of crystal faces, and some related properties. Stereoisomers which are not enantiomorphs are called diastereoisomers, which is often shortened to diamers. Diastereoisomers usually differ in optical rotation and in chemical and physical properties.

Zearalanol can, and does, exist in two diastereoisomeric configurations, one of which has a higher melting point than the other. A mixture of the two diastereoisomers of zearalanol can, for instance, be prepared by the catalytic reduction of the olefinic bond and the ketone group of zearalenone in the presence of hydrogen. This reduction is disclosed in U.S. Pat. No. 3,239,345, issued Mar. 8, 1966. In U.S. Pat. No. 3,697,548, issued Oct. 10, 1972, a procedure is disclosed for the reduction of zearalenone to zearalanol to provide a product which contains a major amount of the high-melting diastereoisomer and a minor amount of the low-melting diastereoisomer of zearalanol.

Both diamers of zearalanol and their derivatives are useful anabolic and estrogenic substances for oral and parenteral administration to animals in the manner disclosed in U.S. Pat. No. 3,239,345. Depending on the intended use for the compound, however, it may be preferred to employ one or the other diamer in a major amount, or even exclusively.

To provide one or the other of the diastereoisomer of zearalanol, the diastereoisomers may be separated. For instance, procedures for separating the higher melting diastereoisomer of zearalanol from a mixture of the high and low melting diastereoisomers are disclosed in Example VI of U.S. Pat. No. 3,239,345, and U.S. Pat. No. 3,687,982, issued Aug. 29, 1972, herein incorporated by reference. When the high-melting diastereoisomer of zearalanol is desired, it is desirable to convert the separated low-melting diastereoisomer of zearalanol to the high-melting diastereoisomer in order to enhance the yield of the high-melting diastereoisomer.

Zearalanol and its derivatives (hereinafter referred to as the zearalanol compounds) may be represented by the structural formula

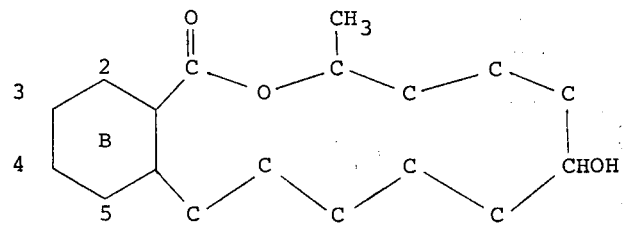

wherein B is a saturated or unsaturated carbon ring, including aromatic ring, and has, as substituents, a member selected from the group consisting of hydrogen, hydroxy, alkoxy, alkanoyloxy, monocyclic aryloxy, and monocyclic arylalkoxy.

The substituents on the B ring are preferably hydrogen, hydroxy, lower alkoxy, e.g., alkoxy containing 1 to about 6 carbon atoms such as methoxy, ethoxy, propoxy, pentoxy, and the like; lower alkanoyloxy, e.g., alkanoyloxy containing 1 to about 6 carbon atoms such as formyloxy, acetoxy, butyroyloxy and the like; monocyclic aryloxy of about 6 to 8 carbon atoms such as phenyloxy, tolyloxy, etc.; or monocyclic arylalkoxy, that is an alkoxy group having an aryl substituent thereon, wherein the alkoxy group has 1 to about 5 carbon atoms and the aryl substituent has about 6 to 8 carbon atoms such as benzyloxy, tolyl methoxy, and the like. The 3 and 5 positions of the B ring can be hydrogen; although, halogen groups, e.g., chloro and bromo, may be substituents at these positions.

The zearalanol compounds exist in two diastereoisomeric forms, the low-melting diastereoisomer of zearalanol and derivatives thereof, hereinafter referred to as the "L" compounds, and the high-melting diastereoisomer of zearalanol and derivatives thereof, hereinafter referred to as the "H" compounds.

In the method of this invention, an L compound is heated in a reaction medium under dehydrogenating conditions in the presence of dehydrogenating amounts of a Raney nickel catalyst to provide dehydrogenated zearalanol, which is then subjected to reducing conditions including the presence of a hydrogen atmosphere under elevated pressure to produce the corresponding H compound. The H compound is usually produced in a mixture with L compound, with the H compound predominating, for instance, the mixture generally contains more than about 50 wt. percent of the H compound, based upon the weight of H and L compounds.

The dehydrogenation of L compound is advantageously conducted in an inert reaction medium, preferably t-butyl alcohol, although other mediums, which will dissolve the L compound and not deleteriously affect the dehydrogenation reaction and subsequent reduction reaction, can be employed. Examples of other mediums include monocyclic aromatics such as benzene and toluene.

In another aspect of the present invention, a hydrogen-acceptor agent can be included in, or, most advantageously, substituted in whole, for the inert medium to enhance the dehydrogenation of L compound. The hydrogen-acceptor can be an acyclic, aliphatic ketone of 3 to about 5 carbon atoms, or carbocyclic ketones containing about 5 to 10 carbon atoms, e.g., acetone, methyl ethyl ketone, cyclohexanone, etc., may be employed. The hydrogen acceptor ketone is employed in hydrogen-accepting amounts and may comprise up to about 100, for instance, often about 0.5 to 70, preferably 1 to 60, percent by weight, of the medium. In a preferred embodiment of the method, the hydrogen-acceptor ketone is employed as the reaction medium in amounts sufficient to accept substantially all of the hydrogen produced during the dehydrogenation.

The medium should be present in at least an equivalent molar basis with the zearalanol compound (i.e., total H and L compounds) and may be used in a substantial excess, for instance, in an amount of about 100 or more times the zearalanol compound by weight. Preferably, the medium is provided in solvent-providing quantities, for instance, in an amount ranging from about 2 to 100, preferably about 5 to 70, times the zearalanol compound by weight.

Water may also be present in the reaction mixture. Generally, the water may be present in an amount of from about 0.01 to 50, preferably about 0.1 to about 25, percent of the reaction mixture based on the weight of the medium. Frequently, the water is present in a minor amount, for instance, in the amounts provided with suspension of the Raney nickel catalyst.

The reaction mixture is subjected to dehydrogenating conditions, including elevated temperatures, for instance, at about 80° to 200°C., preferably about 90° to 180°C., in the presence of dehydrogenation enhancing amounts of Raney nickel catalyst which may be in a suspension of water or lower alkanol. Frequently, the Raney nickel is present in an amount of 0.001 to 10, preferably 0.005 to 5, grams of Raney nickel per gram of zearalanol compound (i.e., total H and L compounds). The dehydrogenation reaction is preferably conducted in an essentially oxygen-free atmosphere, for example, hydrogen, nitrogen, argon or carbon dioxide, to provide a non-oxidizing gaseous atmosphere. The dehydrogenation conditions are maintained for a period of time sufficient to effect dehydrogenation of the L compound. Often, the desired dehydrogenation product is obtained when the dehydrogenating reaction is continued for at least 15 minutes, and preferably, the reaction time is from about 1 to 20 hours. This product is the ketone-derivative of the L compound used, for instance, when the L compound is zearalanol, the ketone-derivative is zearalanone. In an aspect of the present invention, the dehydrogenation step can be used to produce the ketone-derivative as the final product.

The reaction medium is then subjected to reducing conditions to provide H compound. The temperatures employed in the reduction reaction may be in the range from about 50° to 120°C., preferably about 65° to 100°C. The reduction reaction is conducted in the presence of hydrogen gas under elevated pressure, for instance, at about 0 to 5000, preferably about 20 to 1000, psi. The reduction is preferably carried out for a period of at least 15 minutes, and preferably from about 1 to 16 hours to provide the H compound.

The product can then be recovered by any known means. For example, the catalyst can be removed by filtration from the solution while the solution is at a temperature at least sufficient to maintain the zearalanol compounds in solution, for instance, greater than about 10°C. The filtrate can then be concentrated and cooled to crystallize the product. The crystallized product contains the H and L compounds. The amount of H compound to total H and L compounds produced by the method of this invention generally ranges from about 30 to about 65 percent, depending on the selected reaction conditions and other process variables.

The diastereoisomers may be separated by conventional techniques including crystallization. For instance, the zearalanol product may be recrystallized two times from isopropyl alcohol-water mixtures to provide a high-melting product corresponding to the H compound and a low-melting product. A further method of recovering the H compound is by converting the zearalanol to the corresponding 6'-acetate by reaction with acetic acid under esterification temperature, e.g., about 15° to 120°C., then separating the resulting diastereoisomers by fractional crystallization, transesterifying the acetate substituent of the desired fraction with methanol in the presence of a transesterification catalyst, e.g., sulfuric or hydrochloric acid, at about 50° to 65°C., to produce zearalanol.

It may be that the L compound, which is desired to be converted to the corresponding H compound, may have the H compound in admixture therewith. For economic reasons, it is desirable that the zearalanol prepared for treatment by the method of this invention contain less than about 50 percent of the H compound. It is also possible to treat an H compound-rich, zearalanol compound mixture, e.g., where the H compound comprises at least about 75 to 80 weight percent of total zearalanol compound, to provide additional L compound according to the method of this invention. The L compound may be provided in the amount of up to about 35 percent of the zearalanol compound and separated and recovered, if desired.

The zearalanol, or derivative thereof, which may be employed in the method of the present invention, may be prepared in any conventional manner. Zearalanol may be produced from zearalenone which, in turn may be obtained by cultivating the organism Gibberella zeae (Gordon) on a suitable nutrient medium such as is disclosed in U.S. Pat. No. 3,196,019. Zearalanol may be obtained therefrom by reduction of the olefinic bond and the ketone group of zearalenone in the presence of hydrogen. For example, a process for reducing zearalenone to a mixture of zearalanols comprising a major portion of the high-melting diastereoisomers of zearalanol is disclosed in U.S. Pat. No. 3,697,548.

The B ring of zearalanol may be substituted, the hydrogen atom at the hydroxyl groups replaced, or the hydroxyl groups may be removed from the B ring. The B ring may be hydrogenated to provide a saturated ring. U.S. Pat. Nos. 3,239,345; 3,373,033; 3,373,037; and 3,373,039 (all of these patents incorporated herein by reference) disclose zearalanol compounds and processes for making them. The zearalenone obtained by fermentation, as in U.S. Pat. No. 3,196,019, is an S conformer.

The following examples are provided to further illustrate the method of the present invention.

EXAMPLE I

A solution of 15 grams of the low-melting diastereoisomer of zearalanol in 500 milliliters of a reaction medium of t-butyl alcohol and 10 milliliters of acetone is prepared, and 10 grams of Raney nickel catalyst in aqueous suspension is added thereto. The solution is placed under a nitrogen atmosphere and heated to 120°C. in a rocking bomb and is maintained thereat for about 10 hours to provide a dehydrogenated product. The solution is subjected to reducing conditions of a hydrogen atmosphere at about 500 psig and a temperature of about 80°C. for 8 hours, to produce a reduced product. The product is analyzed to contain 53 weight percent of the high-melting zearalanol diastereoisomer.

EXAMPLES II TO V

The procedure of Example I is essentially repeated to provide the high-melting diastereoisomer of zearalanol, except employing the conditions set forth in Table 1.

high-melting diastereoisomer products are provided in Table II.

TABLE I

| Example | Starting Zearalanol Type | Amount (g) | Reaction Medium | Catalyst (g) | Dehydrogenation Conditions | | Reduction Conditions | | Weight percent - high melting diastereoisomer of zearalanol in product |
|---|---|---|---|---|---|---|---|---|---|
| | | | | | Time (hr.) | Temperature °C. | Time (hr.) | Temperature °C. 500 psi | |
| II | low-melting | 15 | 500ml t-BuOH | 10 | 2 | 120 | 8 | 80 | 47 |
| III | low-melting | 15 | 500ml t-BuOH | 10 | 4 | 120 | 4 | 80 | 63 |
| IV | eutectic mixture of high and low melting | 15 | 500ml t-BuOH | 10 | 4 | 120 | 4 | 80 | 63 |
| V | eutectic mixture of high and low melting | 15 | 500ml t-BuOH | 5 | 8 | 120 | 6 | 80 | 58 |

EXAMPLE VI

The procedure of Example I is essentially repeated, except employing a solvent comprising 200 milliliters of t-butyl alcohol and 200 milliliters of acetone to produce a product containing the high-melting diastereoisomer of zearalanol which is recovered.

EXAMPLE VII

The procedure of Example I is essentially repeated, except the solvent contains 10 milliliters of methyl ethyl ketone rather than acetone. A product containing the high-melting diastereoisomer of zearalanol is produced and recovered.

EXAMPLE VIII

The procedure of EXAMPLE I is essentially repeated, except the solvent contains 100 milliliters of water and 500 milliliters of t-butyl alcohol. A product containing the high-melting diastereoisomer of zearalanol is produced and recovered.

EXAMPLES IX TO XIV

The procedure of Example II is essentially repeated, except employing a zearalanol compound having the formula

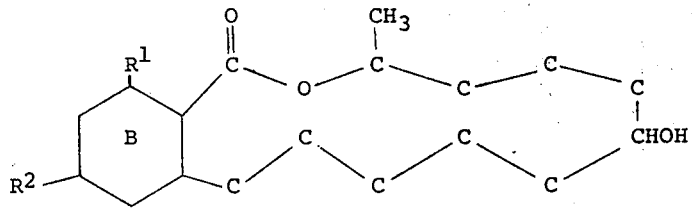

to convert the derivative of the low-melting diastereoisomer to the corresponding derivative of the high-melting diastereoisomer. The values of $R^1$, $R^2$ and B for the

TABLE II

| | PRODUCT CORRESPONDING TO HIGH-MELTING DIASTEREOISOMER OF ZEARALANOL | | |
|---|---|---|---|
| Example | $R^1$ | $R^2$ | B |
| IX | $CH_3O-$ | $CH_3O-$ |  |
| X | $HO-$ | $HO-$ |  |
| XI | $CH_3\overset{O}{\underset{\|}{C}}-O-$ | $CH_3\overset{O}{\underset{\|}{C}}-O-$ |  |
| XII | $HO-$ |  $CH_2-O-$ |  |
| XIII | $H-$ | $H-$ |  |
| XIV | $CH_3CH_2O-$ | $CH_3CH_2O-$ |  |

EXAMPLE XV

To 500 ml. of acetone in a hydrogenation bomb (contained reactor) was added 15.00 g. of the low-melting diastereoisomer of zearalanol and 7.5 g. of a suspension of Raney nickel in water. The bomb was flushed with hydrogen, then sealed and heated 3 hours at 150°C. The catalyst was removed by filtration and the filtrate was concentrated to 100 ml. Slow addition of 500 ml. of $H_2O$, followed by cooling overnight and filtration gave 14.9 g. of crystalline product which analyzed 96.9% of zearalanone of the formula

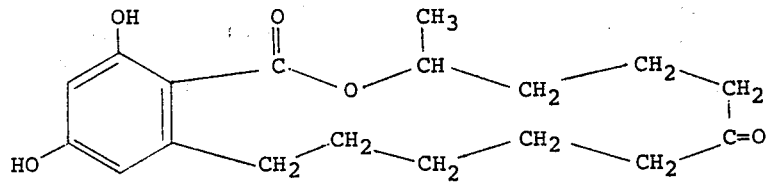

EXAMPLE XVI

A solution of 15 grams of the low-melting diastereoisomer of zearalanol in 500 milliliters of a reaction medium of t-butyl alcohol is prepared and 10 grams of Raney nickel catalyst in aqueous suspension is added thereto. The solution is placed under a hydrogen atmosphere and heated to 120°C. in a rocking bomb and is maintained thereat for about 5 hours to provide a dehydrogenated product. The solution is subjected to reducing conditions of a hydrogen atmosphere at about 500 psig and a temperature of about 80°C. for 4 hours, to produce a reduced product. 10.2 Grams of product is recovered. The product is analyzed to contain 64 weight percent of the high-melting zearalanol diastereoisomer.

EXAMPLE XVII

Five grams of the low-melting isomer of zearalanol and 5 grams of Raney nickel in aqueous suspension were mixed with 75 ml. of t-butyl alcohol. The mixture was stirred and refluxed for 16 hours to dehydrogenate the zearalanol. Subsequently the mixture was subjected to 50 psig of hydrogen pressure for 4 hours at room temperature to reduce the dehydrogenated zearalanol. From this was isolated 4.5 grams of zearalanol containing 55% of the high-melting isomer.

I claim:

1. A method for producing a mixture of zearalanone or its derivatives and corresponding low melting and high melting diastereoisomers of zearalanol or its derivatives comprising dehydrogenating the corresponding low melting diastereoisomer under dehydrogenating conditions, including elevated temperature, in a reaction medium, including dehydrogenating amounts of Raney nickel.

2. The method of claim 1 wherein the reaction medium contains hydrogen-accepting amounts of a hydrogen acceptor ketone.

3. The method of claim 2 wherein the dehydrogenation is conducted under an essentially oxygen-free gas at a temperature from about 80° to 200°C. and the Raney nickel is employed in an amount of about 0.001 to 10 grams per gram of total corresponding zearalanol.

4. The method of claim 3 wherein the hydrogen acceptor ketone is acetone and the oxygen-free gas is hydrogen.

5. A method for producing a mixture of zearalanone and low melting and high melting diastereoisomers of zearalanol comprising dehydrogenating the low melting diastereoisomer of zearalanol under dehydrogenating conditions, including elevated temperature, in a reaction medium containing hydrogen-accepting amounts of a hydrogen acceptor ketone, said medium including dehydrogenating amounts of Raney nickel.

6. The method of claim 5 wherein the reaction is conducted in a contained reactor under an essentially oxygen-free gas at a temperature from about 80° to 200°C., and the Raney nickel is employed in an amount of about 0.001 to 10 grams per gram of total zearalanol.

7. The method of claim 6 wherein the oxygen-free gas is hydrogen and the hydrogen acceptor ketone is acetone.

8. The method of claim 5 wherein the reaction is conducted under refluxing conditions and the medium contains tertiary butyl alcohol.

9. A method for producing the high-melting diastereoisomer of zearalanol or its derivatives from the corresponding low-melting diastereoisomer, comprising dehydrogenating the latter under dehydrogenating conditions, including elevated temperature, in a reaction medium, including dehydrogenating amounts of Raney nickel, to produce a dehydrogenated product and reducing the dehydrogenated product under reducing conditions including the presence of hydrogen under elevated pressure to produce the corresponding high-melting diastereoisomer of zearalanol.

10. The method of claim 9 wherein the dehydrogenation and reduction are conducted in a contained vessel, the dehydrogenation is conducted under an essentially oxygen-free gas at a temperature of about 80° to 200°C. using Raney nickel in an amount from about 0.001 to 10 grams per gram of corresponding zearalanol and the reaction medium contains hydrogen-accepting amounts of a hydrogen acceptor ketone, and the reduction is conducted using hydrogen at a pressure of about 0 to 5000 psi. at a temperature from about 50° to 120°C.

11. The method of claim 10 wherein the oxygen-free gas is hydrogen and the hydrogen acceptor ketone is acetone.

12. A method for producing the high-melting diastereoisomer of zearalanol from the low-melting diastereoisomer of zearalanol comprising dehydrogenating the latter under dehydrogenating conditions, including elevated temperature, in a reaction medium, including dehydrogenating amounts of Raney nickel, to produce a dehydrogenated product and reducing the dehydrogenated product under reducing conditions including the presence of hydrogen under elevated pressure to produce the high-melting diastereoisomer of zearalanol.

13. The method of claim 12 wherein the dehydrogenation and reduction are conducted in a contained vessel, the dehydrogenation is conducted under an essentially oxygen-free gas at a temperature of about 80° to 200°C. using Raney nickel in an amount from about 0.001 to 10 grams per gram of zearalanol and the reaction medium contains hydrogen-accepting amounts of a hydrogen acceptor ketone, and the reduction is conducted using hydrogen at a pressure of about 0 to 5000 psi. at a temperature from about 50° to 120°C.

14. The method of claim 13 wherein the dehydrogenation is conducted using hydrogen as the oxygen-free gas and the hydrogen acceptor ketone is acetone.

15. The method of claim 12 wherein the reaction medium consists essentially of tertiary butyl alcohol, the dehydrogenation is conducted under an essentially oxygen-free gas at a temperature of about 80° to 200°C. using Raney nickel in an amount from about 0.001 to 10 grams per gram of zearalanol, and the reduction is conducted using hydrogen at a pressure of about 0 to 5000 psi. at a temperature from about 50° to 120°C.

16. The method of claim 13 wherein the reaction medium contains tertiary butyl alcohol and the dehydrogenation is conducted under refluxing conditions.

* * * * *